United States Patent [19]

Coon

[11] Patent Number: 4,473,711

[45] Date of Patent: Sep. 25, 1984

[54] LIQUID-PHASE PROCESS FOR OXIDATION OF TETRALIN

[75] Inventor: Robert W. Coon, Charleston, W. Va.

[73] Assignee: Union Carbide Corporation, Danbury, Conn.

[21] Appl. No.: 290,704

[22] Filed: Aug. 6, 1981

[51] Int. Cl.$^3$ .............................................. C07C 45/36
[52] U.S. Cl. .................................... 568/321; 568/819; 568/570
[58] Field of Search ..................... 568/321; 252/431 C

[56] References Cited

U.S. PATENT DOCUMENTS

| | | | |
|---|---|---|---|
| 1,868,531 | 7/1932 | Jaeger | 568/321 |
| 3,404,185 | 10/1968 | Thomas et al. | 568/321 |
| 3,966,821 | 6/1976 | Kudo et al. | 568/321 |
| 4,175,098 | 11/1979 | Mizukami et al. | 568/321 |
| 4,179,402 | 12/1979 | Kim | 252/431 C |

Primary Examiner—James H. Reamer
Attorney, Agent, or Firm—John A. Shedden

[57] ABSTRACT

1-Tetralone, an intermediate in the production of the insecticide, 1-naphthyl carbamate, is conveniently prepared by a liquid phase oxidation of tetralin in the presence of a novel chromium exchanged cation-exchange resin catalyst.

4 Claims, No Drawings

LIQUID-PHASE PROCESS FOR OXIDATION OF TETRALIN

This invention relates in general to an improved liquid-phase process for the oxidation of tetralin to tetralone. In one aspect, this invention is directed to an improved process for the oxidation of tetralin in the presence of a novel chromium-exchanged resin catalyst. In a further aspect the invention relates to an oxidation process which utilizes chromium III exchanged on a gelular, carboxylic acid-type resin in the presence of an aromatic amine catalyst modifier.

BACKGROUND OF THE INVENTION

Prior to the present invention a variety of heterogeneous catalysts have been reported in the literature for oxidation of various organic compounds with gaseous oxygen. For example, an ion-exchanged transition metal catalyst, such as a sulfonic acid-type resin having valence bonded rhodium and vanadium has been disclosed in U.S. Pat. No. 4,021,369 for the oxidation of olefins to epoxy alcohols with gaseous oxygen.

The use of palladium, rhodium or cobalt supported on alumina for tetralin oxidation has been described by A. V. Artimor et al, Russian J. Phys. Chem., 51 (4), 576-7, 1977. However, the selectivity of 1-tetralone is poor with these catalysts.

Heterogeneous catalysts have also been claimed for the liquid-phase oxidation of tetralin as reported in Israeli Pat. No. 41114. High 1-tetralone to 1-tetralol ratios are obtained using a specially prepared insoluble chromium oxide catalyst along with a heterocyclic amine. The catalyst preparation is an involved process and the fine powdery nature of the catalyst could lead to plugging problems in the reactor. Good agitation is needed for the catalyst to be available in the entire reaction zone and hence, packed beds are not very suitable for these gas-liquid reactions.

In contrast, most of the difficulties and disadvantages of the known methods have been overcore by the present invention. The use of the metal exchanged catalyst along with a heterocyclic aromatic amine modifier gives yields and efficiencies comparable to or better than those when the same metals are used in homogeneous form. The metal ion exchanged catalyst is easily prepared by a very simple process using commercially available ion-exchange resins and metal salts and does not necessitate the use of high temperatures.

Accordingly, one or more of the following objects will be achieved by the practice of this invention. It is an object of this invention to provide an improved liquid-phase process for the oxidation of tetralin to tetralone. Another object of this invention is to provide an improved process for the oxidation of tetralin in the presence of a novel metal exchanged cation-exchange resin catalyst. A further object of the invention is to provide a process which utilizes chromium III exchanged on a gelular carboxylic acid-type resin. Another object of this invention is to provide a liquid-phase oxidation of tetralin to 1-tetralone with gaseous oxygen in the presence of a chromium exchanged cation-exchange resin catalyst and an aromatic amine catalyst-modifier. These and other objects will readily become apparent to those skilled in the art in the light of the teachings herein set forth.

DETAILED DESCRIPTION OF THE INVENTION

In its broad aspect the invention relates to an improved process for the oxidation of tetralin to 1-tetralone. The process comprises effecting the oxidation of tetralin in the presence of a catalyst modifier and a catalyst which is comprised of chromium (III) ion exchanged on a gelular carboxylic acid type synthetic cation exchange resin.

Thus, the present invention uses chromium (III) ion exchanged onto a gelular, carboxylic acid-type commercial synthetic resin for the oxidation of tetralin by gaseous oxygen. The catalyst is used as a slurry in the reaction mixture, along with an aromatic amine modifier such as 2-methyl-5-ethyl pyridine, in continuous or batch equipment. A major advantage of this catalyst is that the metal catalyst is not removed with the product but held in the reactor for continuous use, thus reducing catalyst cost as well as eliminating pollution of the environment by toxic metal. Improved efficiencies to desired products and lower efficiency to residues are obtained compared with the soluble chromium carboxylates. Less acids are also produced with the catalyst. Gelular, carboxylic acid-type resin is preferred since it has a higher affinity for Cr(III) ion compared to macroreticular resins or sulfonic acid-type resins.

It has been observed that by using the chromium III ion exchanged gelular carboxylic acid-type synthetic cation exchange resin and a catalyst modifier, such as 2-methyl-5-ethyl pyridine, 1-tetralone was obtained at high efficiencies, i.e., greater than 87 percent. While the ratio of 1-tetralone to 1-tetralol is similar to that obtained with a soluble chromium modified catalyst, it was unexpectedly found that lower efficiency to residue and lower crude product acidity were obtained. For example, it was observed that efficiency to residue was 5-6 percent versus 8-10 percent, and crude product acidity was 0.01 Meq/g versus 0.07 Meq/g when the chromium exchanged resin catalyst was compared with soluble chromium catalyst under similar process conditions. Tetralin hydroperoxide (THP) levels are higher in the case of the chromium exchanged resin catalyst compared to the soluble chromium case. The hydroperoxide levels are lower at higher temperatures and higher MEP levels. Use of macroreticular cation-exchange resin supports also yields lower THP levels. While chromium is readily removed by dilute mineral acid (5-10% aqueous HCl) from macro-reticular sulfonic or carboxylic acid-type resin as well as gelular sulfonic acid-type, chromium could be leached out only by strong HF (40 percent aq) from gelular carboxylic acid-type resins. Chromium exchanged gelular carboxylic acid-type resins also give a slightly higher efficiency to tetralone compared with chromium-exchanged gelular sulfonic or macroreticular carboxylic or macro-reticular sulfonic acid type resins. Although, gelular carboxylic acid type resin is the preferred substrate, the other resins also give results equal to or better than the soluble catalysts and hence are useful for catalyzing tetralin oxidation. High efficiency to tetralone (80-81%) and low efficiency to residue (9%) are obtained with MEP. 2,4-Lutidine, 4-picoline, 3,4-lutidine and 3,5-lutidine are comparable with high tetralone efficiencies (78-79%) and low residue efficiencies (9-11%).

As previously indicated the liquid-phase oxidation of tetraline (neat or in solvents such as acetic acid) by molecular oxygen is known from the literature. The usual products are 1-tetralone, 1-tetralol and higher molecular weight byproducts or mixtures of these with tetraline hydroperoxide. Tetraline hydroperoxide is known to be the primary oxidation product and is in turn converted to the other products thermally or by the action of catalysts.

The distribution of products (1-tetralone, 1-tetralol, residues) depends on the means employed to decompose tetralin hydroperoxide. Thermal decomposition yields a nearly equimolar mixture of 1-tetralone and 1-tetralol. Different catalysts and modifiers yield varying proportion of the major products - 1-tetralone, 1-tetralol - and residue by-products. Usual catalysts employed are the carboxylates of variable - valence transition metals - such as cobalt (III), which gives ketone/alcohol ratios in the range of 1:1-2:1.

of 1-tetralone to 1-tetralol was obtained with chromium. U.S. Pat. No. 3,404,185 teaches the means of obtaining rations of better than 15:1 using a chromium salt-amine complex catalyst. A high ratio of 1-tetralone to 1-tetralol is desirable since 1-tetralone is the more useful intermediate, especially in the manufacture of 1-napthol.

These catalysts are used homogeneously in the reaction medium, i.e., the metal and modifiers are soluble in the reaction mixture. A number of disadvantages are evident due to the solubility of the metal salts. The metal ion used at concentrations of 100-250 ppm is invariably lost with the product and has to be replenished sometimes at a substantial cost. The presence of metal can cause residue generation in the product recovery system as well. Recovery of metal from product is complicated by the need for a complex and quite often inefficient separation from residue byproducts. Recycle of metal along with residues is detrimental, since, some of the residue compounds (quinones, napthols, phenols) are known oxidation inhibitors. Hence, usually, the metal is not recovered for recycle.

The metal exchanged resin catalyst employed in this invention is easily prepared from commercially available materials, i.e., metal salts or metal salt solutions and synthetic cation exchange resins, preferably in the acid form. The catalyst is prepared simply by slurrying the resin in the metal salt solution allowing sufficient time for the metal to exchange, draining the solution, washing the water to remove the excess salt and drying the resin. While the exact nature of metal bonding to active sites on the resin is at present not known, it is believed that metal atoms are bound to three or less acidic active sites. The original ligand (from the salt) may also be present, still attached to the metal atoms.

Commercial synthetic ion-exchange resins are available as spherical beads with sizes distributed in the range of 300 $\mu$m. to 1,400 $\mu$m. Particle size is not critical. Thus the resin may be screened before or after chromium exchange and the desired particle size selected based on equipment. Particle sizes greater than 500 $\mu$m are preferred in equipment where attrition of smaller particles may be a problem.

The catalyst resins used in the process of this invention are preferably used in the form of beads. The metal ion-exchanged resin beads are easily fluidized and hence can be used as a slurry in reactors with mixing by mechanical means or by gas-sparging. The large beads (300-1,200/$\mu$m) afford the use of larger openings in filters or screens on the resin by chemical bondage and does not leach out under process conditions. We have discovered that even strong mineral acids except HF do not readily take out Cr(III), exchanged on gelular, carboxylic acid-types resins. Thus, regeneration of catalyst is not necessary for a considerable period of operation.

As previously indicated, the metal exchanged resin catalyst is used in conjunction with a catalyst modifier. Illustrative of the catalyst modifiers, are the aromatic amines such as 2-methyl-5-ethylpyridine, 2-ethyl-5-methylpyridine, 2,5-diethylpyridine, and the like.

Other suitable amines include aromatic and substituted aromatic amines such as pyridine, $\alpha$picoline, quinoline, and the like - as well as mixtures thereof. Particularly suitable amines are the alkyl-substituted pyridines, especially the lower alkyl substituted pyridines, disclosed in U.S. Pat. No. 3,404,185.

In the process of this invention the chromium exchanged resin catalyst is used as a slurry, at from about 1 to about 20 percent (by weight) in the reaction mixture, and preferably from about 4 to about 6 percent. The concentration of the catalyst modifier, can vary from about 1 percent to about 8 percent, with from about 2 to about 6 percent preferred and from 3 to 5 percent most preferred. The reaction type (i.e., batch, continuous) is most preferably continuous, with continuous, or batched or mixed operation. The reactor type is not critical and any reactor giving good gas-liquid contact in a well mixed slurry with provision for containing the resin within the reactor is operable. Mixing of the liquid and resin particles may be accomplished by mechanical means or properly designed gas-pargers known in the art.

Gaseous oxygen as either pure molecular oxygen, air or an oxygen containing gas is used as oxidant. Of these oxidants, air is most preferred. The moles ratios of reactants, gaseous oxygen to tetralin is most preferably 0.4 to 0.6, preferably 0.2 to 0.6 and operably 0.1 to 1.8. The gaseous oxygen to tetralin should be high enough to enable the desired extent of reaction, preferably below 40 percent tetralin conversion, but should not be sufficiently high to create an unnecessary safety hazard from excessive oxygen breakthrough. The temperature of the process can range from about 80° to about 200° C., with from about 120° to about 170° C. preferred and from about 130° to 150° C. most preferred. The total pressure on the system should be sufficient to maintain liquid phase. The oxygen partial pressure at the point of admixture with the liquid reactants is from about 10 psia to about 50 psia, with about 15 psia to 30 psia preferred. Sufficient oxygen should be provided so that the reaction mixture is not oxygen starved. Very high oxygen partial pressures could become hazardous as explosive mixtures of oxygen and hydrocarbon are formed.

The reaction time for the liquid phase, in a continuous mode of operation, is not ciritcal and varies from about 0.1 to 2.0 hours depending upon the temperature and oxygen partial pressure. A reaction time of about 0.5 hours is preferred. The contact time of gaseous oxygen with liquid can vary from about 0.1 to about 50 seconds depending on the temperature and mixing effect. A contact time from about 2 to 25 seconds is preferred. Gaseous oxygen can be bubbled through the liquid in batch systems for 0.5 to 3 hours. Gaseous oxygen and liquid can be reacted in a closed batch system with sufficient oxygen and reaction time provided to achieve the desired conversion.

No solvents are required in addition to the reactants and catalysts. The concentration of tetralin in the liquid can be the highest convenient concentration in the liquid phase and is not deemed critical. Care should be taken in adding acidic solvents to ensure that chromium will not be exchanged out of the resin by the acid, especially when the macroreticular resins or gelular sulfonic acid resins are used as catalyst supports.

The following examples illustrate the best mode presently contemplated for the practice of this invention:

EXAMPLE 1

Ten grams of chromium acetate (purified reagent grade powder from Matheson, Coleman and Bell Co.) was dissolved in 100 ml of deionized water. The solution was filtered to remove any insoluble material. Twenty five grams of Dowex CCR-2 synthetic ion-exchange resin (Lot No. MM 01104-K2, Dow Chemical Co.) was washed with 3×50 ml of deionized water, filtered under vacuum between the washes. The chromium acetate solution and the washed resin were then mixed together, slurried and allowed to stand for one hour. The mixture was slurried again, the liquid drained and passed over the resin again in a column. The resin was then washed with de-ionized water (350 ml) until the wash water was clear. The resin was then washed with acetone and then dried in a vacuum oven at 60° C. and was green in color.

To a 1" ID 8" long cylindrical glass reactor, fitted with a gas sparger, a magnetic stirrer and a condenser, was charged 5.0 g of chromium exchanged resin prepared above, 25 g of tetralin (99.3 weight percent purity) and 2 g of 2-methyl-5-ethyl pyridine. The reactor with contents was immersed in a hot-oil bath whose temperature was controlled at 120°±2° C. When the temperature of the reactants had risen to 120° C., oxygen flow at 235 standard ml/minute was started. At the end of two hours the reaction mixture analyzed 18.35 percent 1-tetralone, 1.81 percent 1-tetralol, by vapor phase chromatography, giving a 1-tetralone/1-tetralol ratio of 10.1. Tetralin hydroperoxide level was 1.3 percent by weight.

EXAMPLE 2

Operating under similar conditions as in Example 1 without adding resin catalyst using 25 g tetralin and 2 g of 2-methyl-5-ethyl pyridine gave a higher hydroperoxide level (4.9 percent), lower 1-tetralone (16.3 percent) and higher 1-tetralol (2.4 percent) levels. The 1-tetralone to 1-tetralol ratio was 6.7.

EXAMPLE 3

Fifty grams of Amberlite IRC-50 resin (a macroreticular carboxylic acid resin from Rohm & Haas Co.) was exchanged with chromium (III) ion from a 7.5 percent aqueous chromium acetate solution (made by diluting a 50 percent aqueous chromic acetate solution from Shepherd Chemical Co.) by soaking the resin in the solution for 24 hours, washing repeatedly with water, then acetone and finally drying. Forty grams of the dry resin and 1,000 g of refined tetralin (99.3 percent purity) were charged to a 2 liter agitated resin flask reactor immersed in a temperature controlled oil bath, provided with a condenser, a cooling coil and a fritted glass gas sparger. Oxygen, at 2,000 standard ml/min was sparged through the well mixed reaction mixture maintained at 140° C. At the end of 2 hours, 42.6 percent of the tetralin had been converted. The efficiency to 1-tetralol was 23.8 percent and the efficiency to residues was 26.0 percent.

The use of 2-methyl-5-ethyl pyridine at 4 percent level, under the same conditions as above, improves the efficiency to 1-tetralone considerably. Thus, with 4 percent MEP, at the end of 2 hours, the efficiency to 1-tetralone is 83.4 percent, while the efficiency to 1-tetralol is 8.5 percent and the efficiency to residues is reduced to 8.1 percent. Tetralin conversion also decreases to 26.4 percent.

EXAMPLE 4

Two hundred and twenty seven grams of oven dried Dowex CCR-2 resin was exchanged with chromium (III) ion from a 50 percent aqueous chromic acetate solution. The resin gained 20.6 percent in weight due to the exchange. The chromium content was analyzed about 9 percent by weight. Scanning electron micrographs showed uniform distribution of chromium within the spherical resin beads.

Thirty five grams of the chromium-exchanged resin was charged to a jacketed ½" ID×5 ft. stainless steel continuous-pilot- tubular reactor provided with a gas inlet into the tube to lift liquid, gas and resin particles up the tube, a gas-liquid separation section (accumulator) immediately above the tube and a ⅜" tubing downcomer from the accumulator for circulating the catalyst-liquid slurry back to the bottom section. The reaction volume was maintained at 620 cc. A filter was used in the product take-off line to contain the resin within the reactor. The temperature of reaction mixture was controlled at 140° C. and the pressure was controlled at 140 psig. Liquid feed containing 4.8 percent, 2-methyl-5-ethyl pyridine, 93.5 percent tetralin and 1.7 percent naphthalene was fed continuously to the reactor at 1450 ml/hr giving a mean residence time of 26 minutes. Air, from a cylinder was continuously fed to the reactor at 5400 std. ml/min. The reactor was operated in a continuous mode for about 5 hours and then another 5 hours during which time the liquid product was collected. The tetralin conversion was 9.1 percent, with 1-tetralone to 1-tetralol ratio of 11.3. Efficiency to 1-tetralone was 88.6 percent, to 1-tetralol was 5.9 percent and to residue was 5.5 percent. Tetralin hydroperoxide level was 0.82 percent.

The chromium content of the chromium-exchange-resin catalyst had not changed after 175 hours of continuous operation under a wide range of operating conditions. The activity of the catalyst and efficiency also were unchanged.

EXAMPLE 5

Operation in equipment similar to example 1 at a higher temperature (140° C.±1° C.), using 100 g of tetralin, 3.3 g 2-methyl-5-ethyl pyridine and 5 g of Zn(II), Zr(II), Sn(II) or Ag(1) exchanged resin gave tetralin conversion of 19 to 21% with efficiencies of 83-85% to 1-tetralone, 7-9% to 1-tetralol and 6-8% to residues. Tetralin hydroperoxide level was at 1-2% by weight. The 1-tetralone to 1-tetralol ratio was 9-12.

Table I below sets forth results obtained on other catalysts:

TABLE 1

METAL EXCHANGED DOWEX CCR-2 RESIN CATALYST RESULTS FROM OXIDATION[a]

| Metal Ion | Conversion % | Tetralone Tetralol Ratio | % Efficiency to | | | Tetralin Hydroperoxide, % | | |
|---|---|---|---|---|---|---|---|---|
| | | | Tetralone | Tetralol | Residue | 30 min | 60 min | 120 min |
| None[b] | 25.4 | 6.3 | 78.0 | 12.2 | 9.8 | 8.8 | 8.6 | 2.9 |
| None[c] | 24.5 | 7.3 | 77.7 | 10.4 | 11.8 | 7.8 | 7.3 | 2.4 |
| Cu (+2) | 27.0 | 7.9 | 79.0 | 9.9 | 10.8 | 1.2 | 1.2 | — |
| Fe (+3) | 30.7 | 6.2 | 76.0 | 12.2 | 11.9 | 2.5 | 2.0 | |
| Fe (+2) | 34.7 | 4.2 | 69.0 | 16.0 | 15.0 | 7.5 | 7.0 | 2.0 |
| Mn (+2) | 31.3 | 5.4 | 74.8 | 13.7 | 11.5 | 3.8 | 3.3 | |
| Ni (+2) | 22.2 | 7.5 | 79.6 | 10.4 | 9.9 | 4.5 | 5.4 | |
| Co (+2) | 35.0 | 2.6 | 62.1 | 22.2 | 15.7 | 2.0 | 1.0 | |
| Zn (+2) | 19.3 | 9.8 | 85.0 | 8.5 | 6.4 | 1.2 | 1.6 | |
| Sn (+2) | 21.6 | 12.0 | 85.1 | 7.0 | 7.9 | 0.7 | 1.2 | |
| Sb (+3) | 22.3 | 5.5 | 75.6 | 13.6 | 10.8 | 2.2 | 2.1 | |
| Hg (+2) | 23.0 | 7.3 | 80.4 | 11.0 | 8.6 | 5.6 | 4.7 | |
| Ag (+1) | 18.5 | 10.1 | 84.8 | 8.2 | 7.0 | 2.3 | 2.8 | |
| Zr (+2) | 20.9 | 8.7 | 83.2 | 9.4 | 7.3 | 1.0 | 1.6 | |

Notes:
[a]Semi-batch oxidation at 140° C., 100 g tetralin, 4 cc MEP, 5 g resin.
[b]No metal, no resin.
[c]Unexchanged resin
[d]Average of several experiments Although the invention has been illustrated by the preceding examples it is not to be construed as being limited to the materials employed therein, but rather the invention is directed to the generic area as hereinbefore disclosed. Various modifications and embodiments thereof can be made without departing from the spirit and scope thereof.

What is claimed is:

1. A process for the liquid-phase oxidation of tetralin to tetralone wherein the ratio of the desired tetralone to the undersired tetralol is at least about 10 to 1, which process comprises contacting a mixture of tetralin and an aromatic amine catalyst modifier with gaseous oxygen in a mole ratio of oxygen to tetralin of from about 0.1 to about 1.8 in the presence of from about 1 to about 20 weight percent based on the weight of the reaction mixture, of a catalyst consisting essentially of a chromium (III) ion enchanged on a gelular carboxylic acid-type synthetic cation exchange resin.

2. The process of claim 1 wherein said catalyst modifier is an alkyl-substituted pyridine.

3. The process of claim 1 wherein said catalyst modified in 2-methyl-5-ethylpyridine.

4. The process of claim 3 wherein said 2-2methyl-5-ethylpyridine is present in an amount of from about 1 to about 8 weight percent of the reaction mixture.

* * * * *

UNITED STATES PATENT AND TRADEMARK OFFICE
CERTIFICATE OF CORRECTION

PATENT NO. : 4,473,711

DATED : September 25, 1984

INVENTOR(S) : Robert W. Coon

It is certified that error appears in the above-identified patent and that said Letters Patent is hereby corrected as shown below:

Column 1, line 28, "selectivity of" should read -- selectivity to --.

Column 1, line 42, "overcore" should read -- overcome --.

Column 3, line 13, "proportion" should read -- proportions --.

Column 3, after line 17 insert -- Other metal ions and ligands have also been used. The highest ratio --.

Column 3, line 20 "rations" should read -- ratios --.

Column 4, line 11 " a picoline" should read -- α-picoline --.

Column 4, line 30, "gass-pargers" should read -- gas-spargers --.

Column 4, line 54, "ciritcal" should read -- critical --.

Column 6, line 43, "and then another 5 hours" should read -- and then another 1.5 hours --.

UNITED STATES PATENT AND TRADEMARK OFFICE
CERTIFICATE OF CORRECTION

PATENT NO. : 4,473,711

DATED : September 25, 1984

INVENTOR(S) : Robert W. Coon

It is certified that error appears in the above-identified patent and that said Letters Patent is hereby corrected as shown below:

Column 8, line 34, "2-2-methyl" should read - - 2-methyl --.

Signed and Sealed this

Seventh Day of May 1985

[SEAL]

*Attest:*

DONALD J. QUIGG

*Attesting Officer*   *Acting Commissioner of Patents and Trademarks*